United States Patent [19]
Yang et al.

[11] Patent Number: 5,308,592
[45] Date of Patent: May 3, 1994

[54] EQUIPMENT FOR MIXED PHASE REACTION DISTILLATION

[75] Inventors: Zongren Yang; Xingren Hao; Jinshan Wang, all of Shandong, China

[73] Assignee: China Petrochemical Corporation (SINOPEC), Beijing, China

[21] Appl. No.: 912,852

[22] Filed: Jul. 14, 1992

Related U.S. Application Data

[63] Continuation-in-part of Ser. No. 647,892, Jan. 30, 1991, abandoned.

[30] Foreign Application Priority Data

Dec. 3, 1990 [CN] China .............................. 91109526.5

[51] Int. Cl.⁵ .......................... B01J 8/04; B01J 8/02; B01D 11/02; B01D 3/14
[52] U.S. Cl. .................... 422/191; 422/193; 422/211; 422/281; 422/282; 202/158; 203/DIG. 6
[58] Field of Search ............ 422/191, 193, 194, 211, 422/216, 261, 275, 280, 281, 282; 202/158; 203/DIG. 6

[56] References Cited

U.S. PATENT DOCUMENTS

| | | | |
|---|---|---|---|
| 2,555,606 | 6/1951 | Potts .................... | 203/DIG. 6 |
| 2,676,875 | 4/1954 | Barr ..................... | 422/191 X |
| 2,742,347 | 4/1956 | Carlson .................. | 422/193 X |
| 4,471,154 | 9/1984 | Franklin ................ | 203/DIG. 6 |
| 4,475,005 | 10/1984 | Paret .................... | 203/DIG. 6 X |
| 4,568,523 | 2/1986 | Wijffels et al. .......... | 422/191 |
| 4,624,748 | 11/1986 | Haunschild .............. | 203/DIG. 6 |
| 4,847,430 | 7/1989 | Quang et al. ............ | 422/193 X |
| 4,937,051 | 6/1990 | Graven et al. ........... | 422/191 X |
| 5,013,407 | 5/1991 | Nocca et al. ............. | 422/194 X |
| 5,026,459 | 6/1991 | Quang et al. ............ | 422/194 X |

Primary Examiner—Robert J. Warden
Assistant Examiner—Christopher Y. Kim
Attorney, Agent, or Firm—Armstrong, Westerman, Hattori, McLeland, & Naughton

[57] ABSTRACT

Equipment for mixed phase reaction distillation, particularly equipment for mixed phase reaction distillation to produce MTBE. The equipment comprises a rectifying section I at the upper part, a reaction section II at the middle part, and a stripping section III at the lower part. The reaction section II comprises a plurality of superposed catalyst beds which are connected by at least one catalyst flow pipe disposed between each pair of adjacent catalyst beds, and a sealed cover at the top above the uppermost catalyst bed of the plurality of catalyst beds. The reaction section II further comprises at least one vapor passageway disposed at one side of the reaction section II, and at least one liquid passageway disposed at the other side of the reaction section II. The reaction section II also includes one feed inlet disposed between the uppermost catalyst bed and the sealed cover for introducing preheated feed and one feed inlet disposed between each pair of adjacent catalyst beds of the plurality of catalyst beds for introducing unpreheated feed. The equipment may further comprise another reaction section above a lower reaction section.

13 Claims, 3 Drawing Sheets

EQUIPMENT FOR MIXED PHASE REACTION DISTILLATION

This is a continuation-in-part application of our pending U.S. patent application Ser. No. 07/647,892, filed on Jan. 30, 1991, abandoned for "Process for Mixed Phase Reaction Distillation".

FIELD OF THE INVENTION

The present invention relates to equipment for mixed phase reaction distillation, and especially relates to equipment for mixed phase reaction distillation to produce MTBE.

BACKGROUND OF THE INVENTION

It is well known that conventional manufacturing processes conduct the reaction of reactants and the separation of products in reactors and distillation columns separately. Such processes have the following disadvantages: too many operational steps, large investment for the fabrication of equipment, the reaction heat cannot be used and an additional cooling system is needed to take away the reaction heat so as to maintain the reaction temperature constant. When these processes are used for reversible reactions, due to the limited conversion of the equilibrium reaction, such processes need to repeat the reaction-distillation procedure for two or more times to obtain the desired conversion of the reactants.

A catalytic distillation process has been developed to simplify the process mentioned above and to utilize the reaction heat during the reaction-distillation procedure. The reaction of the reactants and the distillation of products are carried out in the same catalytic distillation column, the products being distilled out as soon as they are formed. As a result, the reaction tend equilibrium can be broken which makes the reaction toward completion and increase the conversion of the reactants. In addition, the reaction heat can be absorbed by the evaporation of the reactants. Therefore, not only can the reaction temperature can be maintained constant, but also the energy consumption of the process can be greatly reduced.

A typical catalytic distillation column contains three sections: a rectifying section at the upper part, a catalytic reaction section at the middle part and a stripping section at the lower part of the column. In said column, it is obvious that the stream of liquid phase and the stream of vapor phase flow countercurrently through said catalytic reaction section and undergo reaction and distillation in said section. However, when the particle size of the catalyst is too small, the flow resistance of the catalyst beds will be too great and makes the liquid and vapor streams difficult to pass through the reaction section countercurrently, which causes the reaction-distillation process very difficult to continue.

Several methods for packing catalyst have been developed to solve the above problems. U.S. Pat. No. 3,434,534 teaches to put catalyst into liquid downcomers of distillation trays as additional reactors. According to this process, the amounts of catalyst loaded in said downcomers are limited. U.S. Pat. No. 4,471,154 proposes to use catalyst capsules, in which catalyst is enclosed in a fabric cloth or a cloth of intercrossed stainless wires permeable to liquid but impermeable to catalyst particles having a shape of rectangular or other form, and distribute these capsules on the distillation trays in the distillation column. The reactants diffuse into the capsules and react on the catalyst surface inside the capsules as it flows across the distillation trays. This method also limits the amount of catalyst and does not promote the reaction of the reactants due to the diffusion resistance of the capsules to the reactants and the products. Similarly, U.S. Pat. No. 4,215,011 discloses a method of using catalyst capsules, in which catalyst is in a number of fabric cloth bags, the bags being packed in the catalytic reaction zone with channels between these capsules so that the liquid and vapor can countercurrently flow through said catalytic reaction zone. U.S. Pat. No. 4,847,430 proposes to use a reaction-distillation zone containing at least two superposed and noncontiguous fixed beds of catalyst, wherein passageways are provided for a vapor phase and at least one distillation tray and at least two liquid redistribution trays are between the fixed beds. Reactant in the liquid phase react under the action of catalyst as they flow through catalyst beds downwardly and undertake the heat and mass transfer on the distillation trays. The disadvantages of the method are the complexity of the structure of the column, the limited amount of the catalyst loaded due to the occupation of space by the distribution and distillation trays between said beds, and the lower reaction efficiency due to the reduction of the concentration of reactants and contact time of the reaction materials with the catalyst by mixing the charge of reactants with the liquid materials coming from the rectifying section. U.S. Pat. No. 3,579,309 discloses a "Column for carrying out organic chemical reactions in contact with fine particulate catalyst". According to this patent, a plurality of catalyst receiving reactors are arranged outside the two sides of the column respectively. In nature, it is a column that a plurality of non-contiguous reactors are disposed outside said column and between a plurality of pairs of distillation trays. U.S. Pat. No. 4,089,752 discloses a "Distillation column reactor and process", said column reactor comprising a distillation column containing standard trays with downcomers, a liquid reservoir, whereby liquid from said downcomers enters said reservoir thereby providing increased residence time in said column. It is used for a homogeneous phase reaction. U.S. Pat. No. 4,624,748 discloses "Catalyst system for use in a distillation column reactor", said column including an annularly-defined space within the reactor comprised of vapor-permeable material with packed catalyst and alternately positioned vapor barrier means. In such a system, the flow resistance between upwardly flowing vapor phase and downwardly flowing liquid phase is quite significant; and since the inner and outer wall forming the annularly-defined catalyst bed are perforated plates, and both the vapor and liquid phase can pass through the perforated plates, or liquid may be taken out by vapor phase, which make operation and entire system unworkable.

OBJECTS OF THE INVENTION

As described above, the conventional processes for conducting the reaction of reactants and the distillation of products separately have the following disadvantages: costly investment and maintenance expenses, complicated operation procedure, waste of reaction heat and requirement for an extra cooling system. Although the catalytic distillation processes do conduct the reaction of reactants and the distillation of products in said equipment and the reaction heat can be utilized, the structure of the catalytic distillation section is complicated, the capacity of catalyst loaded is low, the height of the catalytic distillation column is high and the operation is inconvenient. Furthermore, the reaction efficiency is lower due to the mixing of the feed with the liquid coming from the rectifying section.

One object of the present invention is to provide a mixed phase reaction distillation equipment simple in structure, higher catalyst efficiency, and also has lower investment for construction.

Other objects and advantages of the present invention will be described hereinafter.

SUMMARY OF THE INVENTION

The present invention relates to equipment for mixed phase reaction distillation, and especially relates to equipment for mixed phase reaction distillation to produce MTBE. The equipment of the present invention comprises a rectifying section I at the upper part, a reaction section II at the middle part, and a stripping section III at the lower part, wherein said reaction section II comprises:

a) a plurality of superposed catalyst beds (1) which are connected by at least one catalyst flow pipe (7) disposed between each pair of adjacent catalyst beds for making said catalyst continuous;

b) a sealed cover (51) at the top above the uppermost catalyst bed of said plurality of catalyst beds (1) of said reaction section II;

c) at least one means providing a vapor passageway (3) disposed at one side of said reaction section II, and at least one liquid passage way (4) disposed at the opposite side in said reaction section II;

d) one feed inlet (8) between the uppermost catalyst bed and said sealed cover (51) for introducing preheated feed and one feed inlet (e.g., 9a, 9b) disposed between each pair of said plurality of catalyst beds for introducing unpreheated feed.

Alternatively, the equipment of the present invention may further contain another reaction section above the lower reaction section.

The present invention will be described in more detail with reference to the drawings hereinafter.

DETAILED DESCRIPTION OF THE INVENTION

The present invention relates to equipment for mixed phase reaction distillation for the manufacture of ethers by reacting tert-olefins with alcohols, of alkylbenzene by reacting olefins with benzene, of alcohols by reacting olefins with water and of esters by reacting acids with alcohols, and especially relates to equipment for mixed phase reaction distillation for the manufacture of MTBE by reacting tert-butene with methanol.

Figure 1:
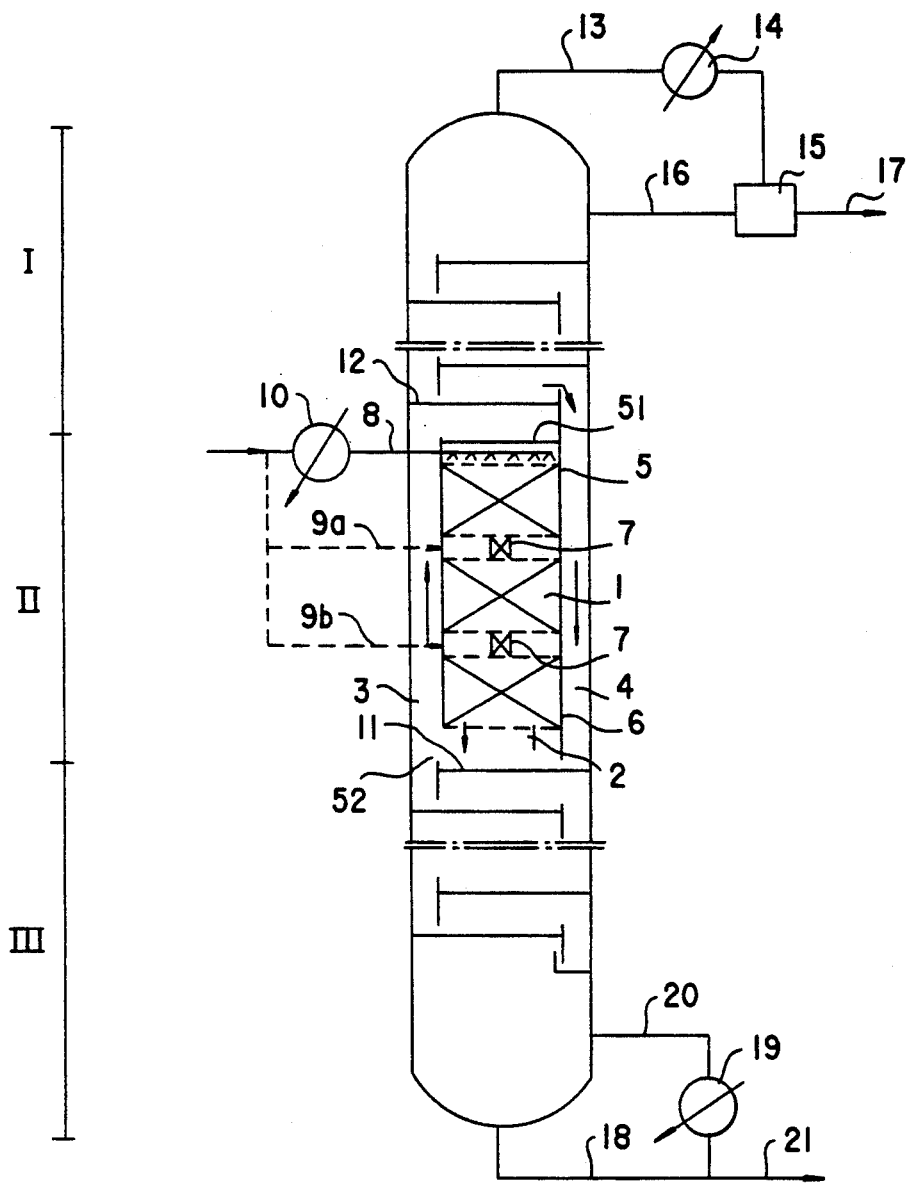
FIG. 1 shows an enclosure of the mixed phase reaction distillation column according to an embodiment of the present invention.

One embodiment of the equipment of the present invention is shown in FIG. 1. As shown in FIG. 1, the equipment comprises a rectifying section I at the upper part, a reaction section II at the middle part, and a stripping section III at the lower part, wherein said reaction section II comprises:

a) a plurality of superposed catalyst beds (1) which are connected by at least one catalyst flow pipe (7) disposed between each pair of adjacent catalyst beds for making the catalyst in said beds continuous;

b) a sealed cover (51) at the top of the uppermost catalyst bed of said plurality of catalyst beds (1) of said reaction section II;

c) at least one means providing a vapor passageway (3) disposed at one side of said reaction section II, and at least one means providing a liquid passage way (4) disposed at the opposite side in said reaction section II;

d) one feed inlet (8) disposed between the uppermost catalyst bed of said plurality of catalyst beds and said sealed cover (51) for introducing preheated feed and one feed inlet (e.g., 9a, 9b) disposed between each pair of adjacent catalyst beds for introducing unpreheated feed.

According to the present invention, the catalyst is packed in bulk in said catalyst beds (1); a catalyst inlet (5) is disposed at the uppermost portion of the uppermost catalyst bed, and a catalyst outlet (6) is disposed at the lowermost portion of the lowermost catalyst bed.

According to the present invention, said reaction section of the equipment also contains conventional elements for a catalytic distillation column, for example, a perforated catalyst-supporting plate or grid (2) at the bottom, and a wire net covered on said plate or grid (2).

According to the present invention, the top of the reaction section II is a sealed cover (51) disposed above said catalyst beds (1). In the case of the higher concentration of reactants in the feed, due to the possible release of the large amount of reaction heat during reaction, said reaction section II contains a plurality of superposed catalyst beds which are connected by at least one catalyst flow pipe (7) disposed between each pair of adjacent catalyst beds for making the catalyst in said catalyst beds continuous.

According to the present invention, the upper end of said means providing a liquid passageway (4) connects with the lowermost tray (12) of said rectifying section I and is higher than said tray (12) to form a weir for maintaining a certain height of liquid layer on said tray (12) and ensuring a complete introduction of the stream of liquid phase into said means providing a liquid passage way (4). The lower end of said passageway (4) is below the upper edge of the weir (52) disposed on the opposite side of the uppermost tray (11) in said stripping section III for preventing the stream of vapor phase from entering into said passageway (4).

According to the equipment of the present invention, the catalyst is packed in bulk in said catalyst beds (1). Therefore, the feed can contact the catalyst effectively, which thereby can promote the reaction. Furthermore, fresh catalyst can be loaded into said plurality of superposed catalyst beds (1) from catalyst inlet (5) disposed at the uppermost portion of the uppermost catalyst bed and via said flow pipes (7), and the deactivated catalyst can be removed from catalyst outlet (6) disposed at the lowermost portion of the lowermost catalyst bed. As a result, the loading and removing of catalyst can be greatly simplified and the investment is greatly reduced. In addition, line (13) is disposed at the top of said rectifying section I for discharging the vapor stream mainly containing the unconverted reactants and line (18) is disposed at the bottom of said stripping section III for withdrawing the liquid stream mainly containing the products.

As a specific example of this equipment, the reaction section only contains one catalyst bed. Catalyst is also packed in bulk in said catalyst bed. The structure thereof is the same as that disclosed above except that no feed inlet(s) are disposed between each pair of adjacent catalyst beds.

When said equipment is adapted for manufacturing the products mentioned above, for example, MTBE, the process thereof comprises the following steps:

1) introducing feed containing reactants preheated by preheater (10) to a temperature sufficient to initiate the reaction, for example, introducing feed containing tert-butene and methanol into said equipment via feed inlet (8);

2) forcing the feed to enter into said reaction section II and to flow downwardly from the top of said reaction section II through said catalyst bed or beds (1) under pressure so as to conduct a reaction among the reactants under the action of catalyst, raising the temperature of reaction mixture by absorbing reaction heat and maintaining the reaction temperature below the boiling point of reactants, allowing the said reaction mixture to flow to the top of said stripping section III;

3) allowing a stream of vapor phase coming from said stripping section III to ascend into said rectifying section I via the means providing a vapor passage way (3) disposed in said reaction section II;

4) allowing a stream of liquid phase coming from said rectifying section I to descend directly onto the uppermost tray of the stripping section III via the means providing a liquid passageway (4) disposed in said reaction section II;

5) discharging a vapor stream mainly containing unconverted reactants from the top of the mixed phase reaction-distillation column via line (13), condenser (14), reflux tank (15), and line (17), at least a portion of the liquid in reflux tank (15) is fed back to the column as reflux via line (16);

6) withdrawing a liquid stream mainly containing the products from the bottom of the mixed phase reaction-distillation column.

When the concentration of reactants in said feed in too high, a larger amount of reaction heat is released, and when the reaction temperature is near the boiling point under the operational pressure, unpreheated feed containing reactants is further added into the catalyst beds via the feed inlet (e.g., 9a) disposed between each pair of the catalyst beds and/or to absorb the reaction heat and further adjust the reaction temperature.

According to the present invention, no redistribution plate or distillation tray is disposed between the adjacent catalyst beds, the total height of the column is greatly lowered. In addition, the temperature in said reaction section II can be controlled, and reaction heat can be highly utilized instead of being taken away via external cooling system, therefore, energy is greatly saved. Furthermore, the liquid phase descending from the rectifying section I enters directly into the stripping section III without passing through the catalyst bed or beds (1) via the means providing a liquid passageway (4) of reaction section II, only feed passes through said catalyst bed or beds (1). Therefore, the catalyst efficiency is greatly increased.

Figure 2:
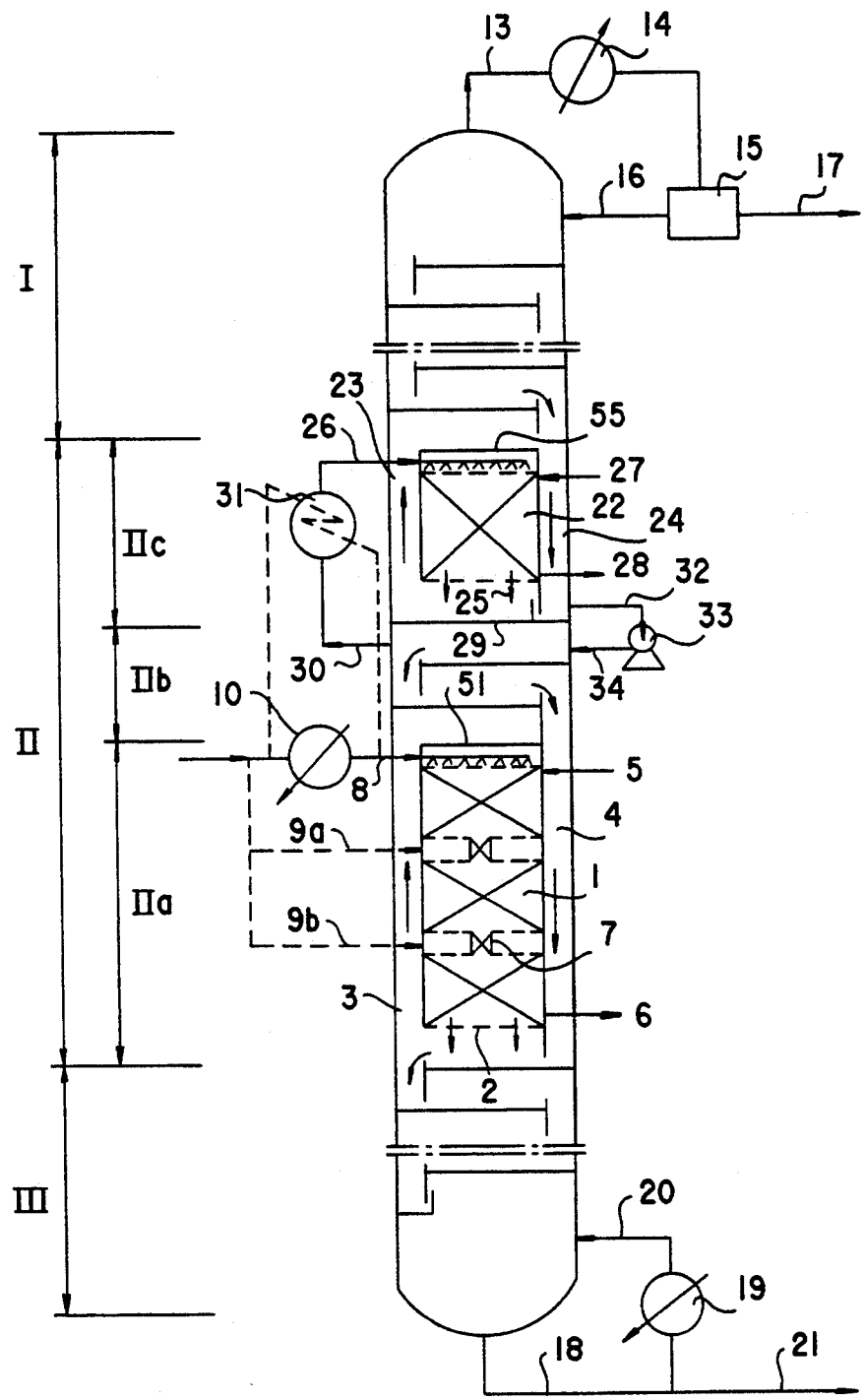
FIG. 2 shows another enclosure of the mixed phase reaction distillation column according to a preferred embodiment of the present invention, which is preferred when high conversion of reactants is required.

According to a preferred embodiment of the present invention, the reaction section II of the equipment contains two reaction zones IIa and IIc. The unconverted reactants in the first reaction zone IIa will continue to react in the second reaction zone IIc. As a result, the overall conversion of reactants of an equilibrium reaction can be further increased. Said equipment for mixed phase reaction-distillation as shown in FIG. 2 comprises a rectifying section I at the upper part, a reaction section II at the middle part and a stripping section III at the lower part, said reaction section II comprises:

a) a lower reaction zone IIa, a middle distillation zone IIb and an upper reaction zone IIc;

b) one catalyst bed or a plurality of superposed catalyst beds which are connected by at least one catalyst flow pipe between each two adjacent catalyst beds for making the catalyst in said plurality of catalyst beds continuous in said lower reaction zone IIa, a catalyst inlet (5) disposed at the uppermost portion of the uppermost catalyst bed and a catalyst outlet (6) disposed at the lowermost portion of the lowermost catalyst bed, a sealed cover (51) at the top above said catalyst bed or above the uppermost catalyst bed of said plurality catalyst beds of said lower reaction zone IIa, a perforated catalyst supporting plate or grid (2) at the bottom of said lower reaction zone IIa, said plate or grid (2) being covered with a wire net;

c) at least one distillation tray in said middle distillation zone IIb, a liquid phase inlet (34) at one side and a vapor phase outlet (30) at the opposite side of the uppermost portion of said zone IIb;

d) one catalyst bed in said upper reaction zone IIc, a sealed cover (55) at the top of said upper reaction zone IIc, a catalyst inlet (27) disposed between the sealed cover and the catalyst bed, and a catalyst outlet (28) disposed at the bottom of said catalyst bed of said zone IIc, a feed inlet (26) disposed at the top of the upper reaction zone IIc, a perforated catalyst-supporting plate or grid (25) at the bottom of said upper reaction zone IIc, said plate or grid (25) is covered with a wire net;

e) a partition (29) disposed between said upper reaction zone IIc and said middle distillation zone IIb, and a liquid phase outlet (32) disposed above said partition (29);

f) at least one means providing a vapor passage way (3) disposed at one side and at least one means providing a liquid passageway (4) disposed at the opposite side in said lower reaction zone IIa; at least one means providing a vapor passageway (23) disposed at one side, and at least one means providing a liquid passageway (24) disposed at the opposite side in said upper reaction zone IIc.

According to the equipment as shown in FIG. 2 of the present invention, there is only one catalyst bed (22) in the upper reaction zone IIc, and there is a partition (29) disposed between the upper reaction zone IIc and the middle distillation zone IIb. A catalyst inlet (27) is disposed at the uppermost portion, and a catalyst outlet (28) is disposed at the lowermost portion of said catalyst bed (22) in said zone IIc. The catalyst is packed in bulk in said catalyst bed (22). The fresh catalyst is loaded via the catalyst inlet (27) and the used, deactivated catalyst is removed from the catalyst outlet (28). At least one distillation tray is disposed in the middle distillation zone IIb for separating the product and the unconverted reactants therein. In the lower reaction zone IIa, the catalyst is also packed in bulk in said catalyst bed or beds (1). The fresh catalyst is loaded into said catalyst bed or beds (1) via said catalyst inlet (5) and the used, deactivated catalyst is removed from said catalyst bed or beds (1) via said catalyst outlet (6).

According to the present invention, the stream of vapor phase coming from said zone IIb is discharged from line (30) and transfers heat with the unpreheated feed in heat exchanger (31), then reintroduced into said zone IIc from the top via line (26) and forced to flow downwardly through said bed (22) of zone IIc. The feed after heat transfer is introduced into the catalyst bed or beds (1) in said zone IIa via line (8).

According to the present invention, the upper end of said means providing a liquid passageway (4) disposed in said lower reaction zone IIa is higher than the lowermost distillation tray of said middle distillation zone IIb to form a weir for maintaining a certain height for the liquid layer on said tray and ensuring all the liquid phase on the lowermost tray of said zone IIb flows into said means providing a liquid passageway (4). A weir is provided on the uppermost tray of said stripping section III for maintaining a certain height for the liquid layer on said tray and ensuring the all stream of vapor phase flows into the means providing a vapor passage way (3) disposed in said lower reaction zone IIa by disposing the lower end of said liquid passage way (4) disposed in said lower reaction zone IIa below the upper edge of said weir on the opposite side of said uppermost tray.

According to the present invention, the upper end of said means providing a liquid passageway (24) disposed in said upper reaction zone IIc is higher than the lowermost tray of said rectifying section I to provide a weir on said lowermost tray for ensuring a liquid layer on said tray. A weir is provided on partition (29), and the lower end of said means providing a liquid passage way (24) disposed in said upper reaction zone IIc is lower than the upper edge of said weir disposed on said partition (29) so as to form a liquid seal.

When the lower reaction zone IIa contains a plurality of catalyst beds, one feed inlet (e.g., 9a and 9b) is disposed between each pair of adjacent catalyst beds of said plurality of catalyst beds for introducing unpreheated feed.

When the said equipment is used for producing the above-mentioned products, the process thereof comprises the following steps:

1) introducing preheated feed containing reactants at a temperature sufficient to initiate reaction into said equipment via feed inlet (8);

2) forcing the feed to flow downwardly through the catalyst bed or beds (1) of the lower reaction zone IIa from the top of the catalyst bed or beds (1) under pressure so as to conduct a reaction among the reactants under the action of the catalyst, reaction heat being used for raising the temperature of the reaction mixture, the reaction mixture flowing downwardly into the top of said stripping section III;

3) allowing a stream of vapor phase coming from the top of said stripping section III to ascend into said middle distillation zone IIb via the means providing a vapor passage way (3) disposed in said lower reaction zone IIa;

4) discharging the stream of vapor phase separated in said middle distillation zone IIb from the top of said zone IIb via outlet (30) and liquefying said discharged stream of vapor phase in a proportion of about 20 to about 50 percent by weight in heat exchanger (31) between said discharged stream of vapor phase and unpreheated feed;

5) introducing the partially liquefied stream of vapor phase in step 4) into the top of said upper reaction zone IIc via inlet (26) and allowing the partially liquefied stream to flow downwardly through the catalyst bed (22) of said zone IIc under pressure for further converting the unconverted reactants under the action of catalyst in said zone IIc;

6) allowing the stream of vapor phase after the reaction of the partially liquefied stream in said upper reaction zone IIc to flow out from the bottom of the catalyst bed, and to ascend into said rectifying section I via means providing a vapor passageway (23);

7) withdrawing the stream of liquid phase after the reaction of the partially liquefied stream in the same zone IIc, together with the stream of liquid phase coming from said rectifying section I and descending via said means providing a liquid passageway (24) disposed in said zone IIc via the liquid outlet (32) disposed at the lower portion of said zone IIc, pump (33) and liquid phase inlet (34) disposed at the upper portion of said distillation zone IIb, and circulating the stream of liquid phase into the uppermost distillation tray of said middle distillation zone IIb;

8) distilling the stream of liquid phase entered into said zone IIb, allowing the stream of liquid phase after distillation to descend into the top of said stripping section III via means providing a liquid passage way (4) disposed in said zone IIa;

9) discharging the vapor stream mainly containing the unconverted reactants from the top of said column;

10) withdrawing the liquid stream mainly containing the products from the bottom of said column.

Similar to the process mentioned above, unpreheated feed containing reactants is introduced into the space between the catalyst beds via the feed inlets (9a, 9b) for controlling the reaction temperature in said zone IIa when the concentration of reactants in the feed is too high.

The vapor stream discharged from the top of said column is condensed in condenser (14) and enters into reflux tank (15), at least a part of the liquid in said tank (15) is fed back to the top of said column as reflux via line (16), and the rest liquid in said tank (15) is withdrawn via line (17). Similarly, the liquid phase is withdrawn from the bottom of said column via line (18), at least a part of said liquid phase is vaporized in the reboiler (19) and then fed back into the bottom of said column via line (20), and the rest liquid is withdrawn from said column via line (21).

It should be understood that different feed should be used for producing different products. For example, feed containing tert-butene and methanol is used for producing MTBE; feed containing olefins and water is used for producing alcohols; and feed containing acids alcohols is used for producing esters; feed containing olefins and benzene is used for producing alkyl benzene, etc.

By using the preferred equipment of the present invention for manufacturing methyl tert-butyl ether (MTBE), the conversion of reactants can be higher than 99.0 percent, in a single column. For example, the conversion of tert-butene is higher than 99.5 percent by weight by reacting the $C_4$-fraction containing tert-butene with methanol, i.e., the remaining $C_4$-fraction contains less than 0.5 percent by weight of tert-butene. Said remaining $C_4$-fraction can be used as the raw material for manufacturing high purity butadiene or high purity butene-1.

The equipment as shown in FIG. 2 has the same advantages as those of FIG. 1. In addition, a conversion higher than 99% can be obtained by using the equipment of FIG. 2.

Figure 3:
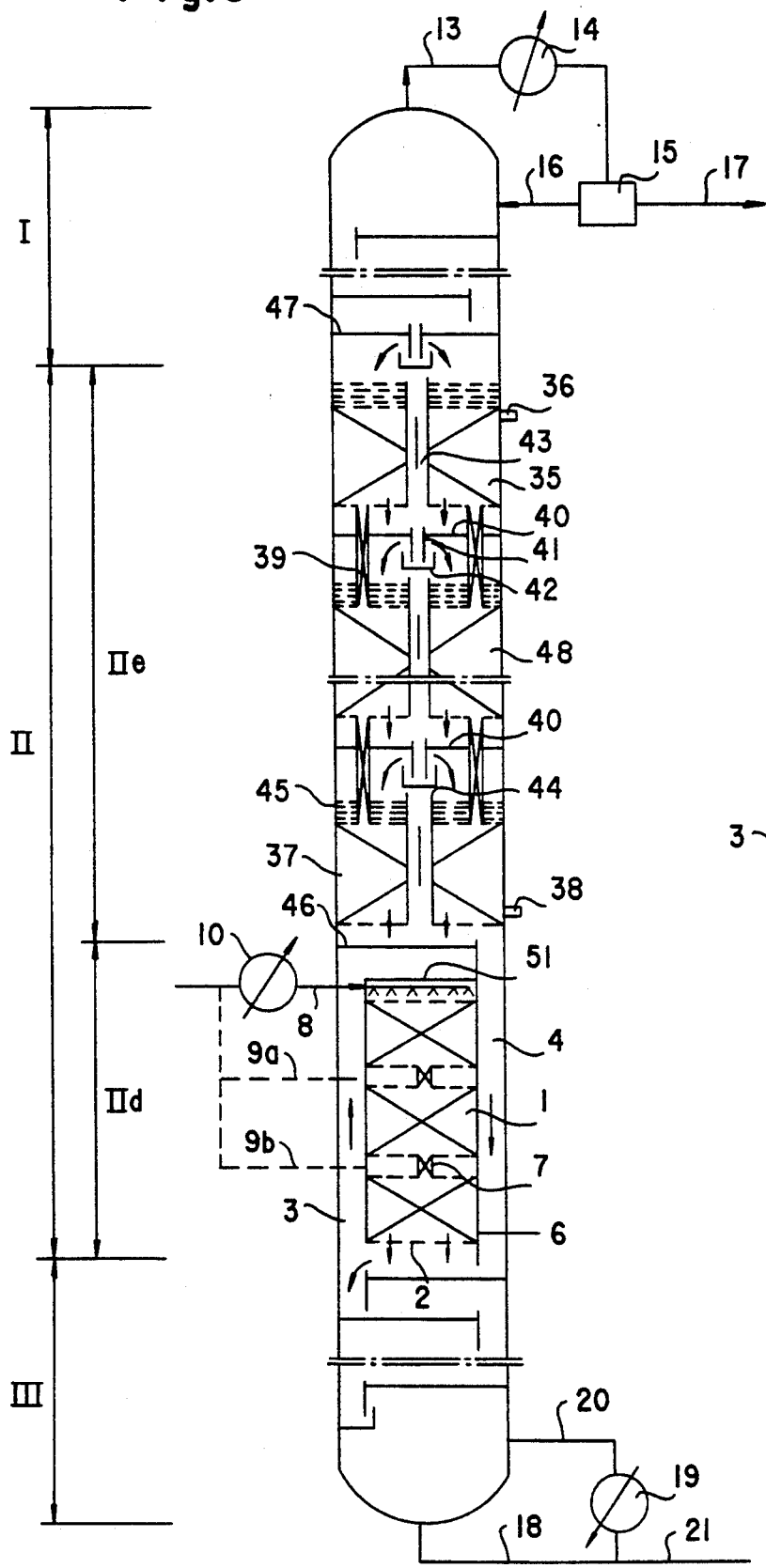
FIG. 3 shows a reaction distillation column, wherein the reaction section comprises a reaction zone and a catalytic reaction distillation zone above said reaction zone, which is also particularly preferred when high conversion of reactants is required.
Figure 4:
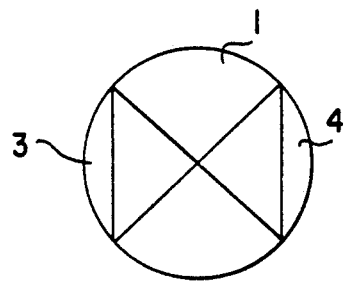
FIG. 4 shows the enclosure in cross-section at the reaction section in the mixed phase reaction distillation column.

According to the present invention, the advantages can be further enhanced by disposing a catalytic reaction distillation zone of the prior art above the reaction section shown in FIG. 1. As shown in FIG. 3, the equipment comprises a rectifying section I, a reaction section II which contains a catalytic reaction distillation zone IIe and a reaction zone IId, and a stripping section III; and said reaction zone IId contains:

a) a plurality of superposed catalyst beds (1) which are connected by at least one catalyst flow pipe (7) disposed between each pair of adjacent catalyst beds for making the catalyst in said catalyst beds of said zone IId continuous;

b) a sealed cover (51) above the uppermost catalyst bed of said plurality of catalyst beds of said reaction zone IId;

c) at least one means providing a vapor passageway (3) disposed vertically at one side in said reaction zone IId, and at least one means providing a liquid passageway (4) disposed vertically at the opposite side in said reaction zone IId;

d) one feed inlet (8) disposed between the uppermost catalyst bed and said sealed cover (51) for introducing preheated feed and one feed inlet (e.g., 9a, 9b) disposed between each pair of adjacent catalyst beds for introducing unpreheated feed.

e) at least one distillation tray (46) between the catalytic reaction distillation zone IIe and the reaction zone IId.

It can be seen from above that the essential structure of reaction zone IId is the same as that of FIG. 1. Similarly, said zone IId can also contain only one catalyst bed. The catalytic reaction distillation zone IIe can be any one of the prior art. As an example of the catalytic reaction distillation zone IIe (as shown in FIG. 3, it comprises:

a) a plurality of superposed catalyst beds (35, 46, 37), at least one catalyst flow pipe (39) disposed between the adjacent catalyst beds, a catalyst inlet (36) disposed at the uppermost portion of the uppermost catalyst bed (35), a catalyst outlet (38) disposed at the lowermost portion of the lowermost catalyst bed (37);

b) at least one distillation tray (40) disposed between each pair of adjacent catalyst beds, a downcomer (41) and a liquid seal trough (42) disposed on the center of each of said distillation trays (40);

c) at least one means providing a vapor passageway (43) in each of said plurality of catalyst beds with a weir (44) which is about 100 to about 300 mm, preferably about 150 to about 200 m, higher than the surface of the catalyst in each of said plurality of catalyst beds to maintain a liquid layer (45) above the catalyst bed.

In the equipment as shown in FIG. 3, the catalyst is packed in bulk in the catalyst beds of said catalytic reaction distillation zone IIe and said reaction zone IId. The fresh catalyst is loaded into each catalyst bed of said plurality of catalyst beds via the catalyst inlets (5, 36) and flow pipes (7, 39) and the used, deactivated catalyst is removed from said catalyst beds via the catalyst outlets (6, 38). The amount of catalyst and the number of the catalyst beds of said catalytic reaction distillation zone IIe depend on the requirements of the conversion. The height of the liquid layer on each of said plurality of superposed catalyst beds is maintained at a height of about 50 to about 200 mm by choosing suitable operation conditions. Therefore, the liquid phase can be uniformly distributed in each of said plurality of catalyst beds of said zone IIe.

When the equipment shown in FIG. 3 is used for producing the products mentioned above, the preheated feed containing reactants firstly enters into the reaction zone IId via inlet (8) and flows downwardly through the catalyst bed or beds, wherein the reaction takes place under the action of the catalyst, the reaction mixture flows onto the top of the stripping section III, the vapor phase stream coming from the stripping section III and containing unconverted reactants flows upwardly into the catalytic reaction distillation zone IIe via the means providing a vapor passageway (3) disposed at the reaction zone IId, the vapor phase stream entering into said zone IIe flows through the catalyst beds via the means providing a vapor passageway (43) and conducts heat and mass transfer with the liquid phase stream flowing downwardly on the distillation tray disposed between each pair of adjacent catalyst beds in said zone IIe, the liquid phase stream after heat and mass transfer flows downwardly through the catalyst beds below the trays and conducts a reaction under the action of the catalyst in said zone IIe; while the vapor phase stream after heat and mass transfer continues to flow upwardly. In this way, the reaction-distillation takes place in the superposed catalyst beds and the distillation trays disposed between each pair of adjacent catalyst beds in said zone IIe for several times until the reaction approaches to completion. Thus, the conversion of reactants of an equilibrium reaction an be increased to higher than 99.0 percent. For example, when the equipment as shown in FIG. 3 is adapted for to the production of MTBE by reacting a $C_4$-fraction containing tert-butene with methanol, about 90–95 percent of tert-butene is converted in the reaction zone IId, then the unconverted tert-butene coming from said zone IId further reacts with methanol in catalytic reaction distillation zone IIe, and the total conversion of tert-butene may be up to 99.0 percent in the same equipment. Therefore, the number of catalyst beds and the stages of the distillatin trays disposed between each pair of adjacent catalyst beds in said zone IIe can be reduced remarkably and the structure of the catalytic distillation column can be simplified.

When this equipment as shown in FIG. 3 is adapted for the manufacture of MTBE by reacting a $C_4$-fraction containing tert-butene with methanol, the conversion of tert-butene is higher than 99.0 percent by weight, i.e., the tert-butene content in the remaining $C_4$-fraction after the reaction is less than 0.5 percent by weight, and the remaining $C_4$-fraction can be used as raw material for manufacturing high purity butene-1 or the raw material for manufacturing high purity butadiene by the method of oxydehydrogenation.

Like all of the equipment of the present invention, the equipment as shown in FIG. 3 can also be used, in addition to the manufacture of MTBE, for the manufacture of other ethers by reacting tert-olefins with alcohols, of alkyl-benzene by reacting olefins with benzene, of alcohols by reacting olefins with water, and of esters by reacting acids with alcohols.

When the equipment as shown in FIG. 3 is used for manufacturing MTBE, the reaction conditions are as follows: operational pressure in the range of about 0.4 to about 2.0 MPa, preferably in the range of about 0.5 to 1.2 MPa, reaction temperature in the range of about 30° to about 120° C., preferably in the range of about 40° to about 90° C., and L.H.S.V, in the range of about 0.5 to about 15 hr$^{-1}$, preferably in the range of about 1.0 to about 10 hr$^{-1}$.

It is advantageous that when the equipment of the present invention is used for producing the products mentioned above, only the feed flows through the catalyst bed or beds of the reaction section or zones. Contrasted to the ordinary catalytic distillation technology, the stream of liquid phase from the rectifying section directly descends into the stripping section via the means providing a liquid passageway and does not flow through the catalyst beds in said reaction section or zone. If the amount of the feed is F, the amount of reflux of the column is R, the amount of the liquid flowing through the catalyst beds below the feed line will be R+F according to an ordinary catalytic distillation process, and the efficiency of the catalysts is proportional to F/R+F; while the amount of the material flowing through the catalyst bed or beds is only the amount of the feed F according to the present invention.

On the other hand, the stream of vapor phase coming from the stripping section III ascends into the rectifying section directly by the means providing a vapor passageway, which solves the problems of the resistance caused by the countercurrent flow of the ascending stream of vapor phase and the descending stream of liquid phase through the catalyst beds and is more favorable for conducting reaction and distillation.

Therefore, the efficiency of the catalyst in the equipment of the present invention is higher than that of the ordinary process of the prior art; the amount of catalyst needed in the equipment of the present invention for achieving the same conversion is 30-50% lower than that needed in the prior art; the total height of the equipment of the present invention is greatly lowered, thus the investment for construction is 15-30% lower than that of the prior art; the energy consumption is 15-30% lower than that of the prior art; and maintenance expense is greatly reduced.

EXAMPLES

The equipment of the present invention will be now described more in detail by way of illustrative and non-limiting examples with reference to the manufacture MTBE by reacting tert-butene with methanol in the presence of sulfonated resin catalyst.

EXAMPLES 1-4

The equipment shown in FIG. 1 of the present invention is used to manufacture MTBE by reacting a C$_4$-fraction containing tert-butene with methanol. The mixed phase reaction distillation equipment used in Examples 1 and 2 are relatively small being 25 mm in diameter and 2 m in height. The amount of the catalyst loaded in each of said columns is 290 ml (dry), and the feed is a C$_4$ hydrocarbon fraction, containing 40 percent by weight of tert-butene. The columns used in Examples 3 and 4 are pilot plant sized of 100 mm in diameter, and 7 m in height. The amount of the catalyst loaded in each of said columns is 1.5 liters (dry), the feed of C$_4$-hydrocarbon fraction contains 36.4 percent by weight of tert-butene. All these Examples use an s-type sulfonated resin catalyst having a particle size in the range of about 0.3 to about 1.3 mm. The operational conditions and results are shown in Table 1.

As shown in Table 1, under the reaction conditions of a pressure of 0.8 MPa a space velocity of 4-8 hr, more than 90 percent by weight of the tert-butene in the C$_4$-fraction is converted after reaction by using the equipment of the present invention. The vapor stream discharged from the top of said column contains less than 4 percent by weight of tert-butene, less than 100 ppm MTBE, which can be used as the feed for alkylation. The liquid stream withdrawn from the bottom of said column contains more than 98 percent by weight of MTBE.

EXAMPLES 5-7

The equipment as shown in FIG. 2 of the present invention is used to manufacture MTBE by reacting a C$_4$-hydrocarbon fraction containing 36.4 percent by weight of tert-butene with methanol. Said column is 100 mm in diameter and 9 m in height. The overall amount of s-type sulfonated resin catalyst having larger pore size which is loaded in said column is 4.8 liters (dry). Under the reaction conditions of a pressure of 0.9 MPa, a reaction temperature of a 40°-80° C., and a L.H.S.V. of 6.2-7.0 hr in the lower reaction zone and pressure of 0.9 MPa, reaction temperature of 77°-82° C., and a L.H.S.V. of 2.3-2.6 hr$^{-1}$ in the upper reaction zone, more than 99 percent by weight of the tert-butene in the C$_4$-fraction is converted into MTBE. The vapor stream, which may be used as the feed for manufacturing butene having high purity or the feed for manufacturing high purity butadiene by the method of oxydehydrogenation, discharged from the top of the column contains less than 0.5 percent by weight of tert-butene and less than 100 ppm MTBE. The liquid stream withdrawn from the bottom contains more than 98 percent by weight of MTBE. The results are shown in Table 2.

EXAMPLES 8-9

The equipment of the invention is used to manufacture MTBE by reacting a C$_4$-hydrocarbon fraction containing 36.6 percent by weight of tert-butene with methanol in the mixed phase reaction-distillation column as shown in FIG. 3. Said column is 100 mm in diameter and 12 m in height. The amount of catalyst loaded in said column is 6.3 liters (dry). The operation conditions and results are shown in Table 3.

As shown in Table 3, under the reaction conditions of pressure of 0.95-0.96 MPa, a temperature of 40°-81° C., and an overall L.H.S.V. of 1.8-1.85 hr$^{-1}$, the conversion of tert-butene in the feed is more than 99 percent by weight. The stream of vapor phase discharged from the top contains less than 0.5 percent by weight of tert-butene, which can be used as feed for manufacturing high quality butene-1 or as feed for manufacture butadiene having high purity. The stream of liquid phase withdrawn from the bottom contains more than 98.0 percent by weight of MTBE.

As modifications may be made in the embodiments herein described without departing from the scope of the invention, it is intended that all matter contained in the foregoing description shall be interpreted as illustrative rather than limiting.

TABLE 1

The manufacture of MTBE by using the equipment shown in FIG. 1

| | Example | | | |
|---|---|---|---|---|
| | 1 micro | 2 micro | 3 pilot | 4 pilot |
| The content of isobutene in feed, wt. % | 40 | 40 | 36.4 | 36.4 |
| Charge of feed l/hr | 1.68 | 2.77 | 5.9 | 7.2 |
| Alcohol/olefin (mole) | 1.05 | 1.05 | 1.11 | 1.12 |
| L.H.S.V., h$^{-1}$ | 4.2 | 6.93 | 7.5 | 8.2 |
| Operation pressure MPa (absolute) | 0.81 | 0.82 | 0.85 | 0.80 |
| Reaction temperature °C. | 40–80 | 40–82 | 40–82 | 40–80 |
| Products from the top, wt. % | | | | |
| MTBE, ppm | <100 | <100 | | |
| isobutene, wt. % | 2.39 | 2.01 | 2.71 | 3.85 |
| Products from the bottom, wt. % | | | | |
| Methanol + C$_4$ | 2 | 2 | 2 | 2 |
| MTBE | 98 | 98 | 98 | 98 |

TABLE 2

The manufacture of MTBE by using the equipment shown in FIG. 2

| | | Example | | |
|---|---|---|---|---|
| | | 5 | 6 | 7 |
| In the lower mixed phase reaction zone IIa | LHSV, h$^{-1}$ | 6.6 | 6.2 | 7.0 |
| | The content of isobutene in feed, wt. % | 36.4 | 36.4 | 36.4 |
| | Alcohol/olefin (mole) | 1.2 | 1.2 | 1.2 |
| | Operation pressure, MPa (absolute) | 0.9 | 0.9 | 0.9 |
| | Reaction temperature, °C. | 40–80 | 40–80 | 40–80 |
| In the upper mixed phase reaction zone IIc | LHSV, h$^{-1}$ | 2.5 | 2.3 | 2.6 |
| | Reaction temperature, °C. | 77–78 | 78–79 | 79–82 |
| | Products from the top, wt. % | | | |
| | MTBE, ppm | <100 | <100 | <100 |
| | Isobutene | | | |
| | Products from the bottom, wt. % | | | |
| | Methanol | 0.94 | 1.12 | 1.05 |
| | C$_4$ | 0.46 | 0.58 | 0.45 |
| | MTBE | 98.60 | 98.30 | 98.50 |
| | The overall conversion of isobutene | 99.53 | 99.14 | 99.23 |

TABLE 3

The manufacture of MTBE by using the equipment shown in FIG. 3

| | Example | |
|---|---|---|
| | 8 | 9 |
| The content of isobutene in feed, wt. % | 36.70 | 36.70 |
| Alcohol/olefin, (mole) | 1.2 | 1.2 |
| Charge of feed (l/hr.) | 7.2 | 7.4 |
| LHSV, h$^{-1}$ | 1.80 | 1.85 |
| Operation pressure, MPa (absolute) | 0.95 | 0.96 |
| Reaction temperature, °C. | 40–80 | 40–81 |
| Products from the top | | |
| Isobutene, wt. % | 0.29 | 0.27 |
| MTBE, ppm | <100 | <100 |
| Products from the bottom | | |
| MTBE, wt. % | 98.25 | 98.74 |
| Methanol, wt. % | 1.34 | 1.02 |
| C$_4$, wt. % | 0.41 | 0.24 |
| The conversion of isobutene, wt. % | 99.48 | 99.52 |

What is claimed is:

1. An equipment for mixed phase reaction distillation having a column with an upper part, a middle part and a lower part, the equipment comprising: a rectifying section I containing a plurality of distillation trays including a lowermost tray at the upper part, a reaction section II at the middle part, a stripping section III containing a plurality of distillation trays including an uppermost tray at the lower part, wherein said reaction section II comprises:

a) a plurality of superposed catalyst beds including an uppermost catalyst bed and a lowermost catalyst bed which are connected by at least one catalyst flow pipe disposed between each pair of adjacent catalyst beds;

b) a sealed cover above the uppermost catalyst bed of said plurality of catalyst beds in said reaction section II;

c) at least one means providing a vapor passageway disposed at one side in said reaction section II, and at least one means providing a liquid passageway disposed vertically at the opposite side in said reaction section II;

d) one feed inlet disposed between the uppermost catalyst bed and said sealed cover for introducing preheated feed from a preheater and at least one feed inlet disposed between each pair of said catalyst beds for introducing unpreheated feed.

2. An equipment according to claim 1, wherein an upper end of said means providing a liquid passageway is higher than the lowermost tray of said rectifying section I to provide a weir on said lowermost tray for ensuring a liquid layer on said tray.

3. An equipment according to claim 1, wherein said plurality of trays of stripping section III includes an uppermost tray and a weir is provided on the uppermost tray of said stripping section for maintaining a height of liquid layer on said tray and ensuring the all stream of vapor phase flows into the means providing a vapor passageway by disposing a lower end of said means providing a liquid passageway below an upper edge of said weir on the opposite side of said uppermost tray.

4. An equipment according to claim 1, wherein catalyst is packed in bulk in said catalyst beds.

5. An equipment for mixed phase reaction distillation having a column with an upper part, a middle part and a lower part, the equipment comprising: a rectifying section I containing a plurality of distillation trays including a lowermost tray at the upper part, a reaction section II at the middle part, and a stripping section III containing a plurality of distillation trays including an uppermost tray at the lower part, wherein said reaction section II comprises:

a) one catalyst bed;

b) a sealed cover above said catalyst bed of said reaction section II;

c) at least one means providing a vapor passageway disposed vertically at one side in said reaction section II, and at least one means providing a liquid passageway disposed vertically at the opposite side in said reaction section II; and d) one feed inlet disposed between said sealed cover and said catalyst bed for introducing preheated feed from a preheater.

6. An equipment according to claim 5, wherein catalyst is packed in bulk in said catalyst bed.

7. An equipment for mixed phase reaction distillation having a column with an upper part, a middle part and a lower part, the equipment comprising: a rectifying section I containing a plurality of distillation trays including a lowermost tray at the upper part, a reaction section II at the middle part and a stripping section III containing a plurality of trays including an uppermost tray at the lower part, wherein said reaction section II comprises:

a) a lower reaction zone IIa, a middle distillation zone IIb, and an upper reaction zone IIc;

b) said lower reaction zone IIa including one catalyst bed or a plurality of superposed catalyst beds which are connected by at least one catalyst flow pipe disposed between each pair of adjacent catalyst beds, a sealed cover above said catalyst bed or above an uppermost catalyst bed of said plurality catalyst beds of said lower reaction zone IIa;

c) said middle distillation zone IIb including at least one distillation tray and a liquid phase inlet at one side and vapor phase outlet at the opposite side of the uppermost portion of said zone IIb;

d) said upper reaction zone IIc including one catalyst bed and a top, a sealed cover above said catalyst bed of said upper reaction zone IIc, a feed inlet disposed between said catalyst bed and said sealed cover at the top of the upper reaction zone IIc:

e) a partition disposed between said upper reaction zone IIc and said middle distillation zone IIb, and a liquid phase outlet disposed above said partition; and f) at least one means providing a vapor passageway disposed vertically at one side and at least one means providing a liquid passageway disposed vertically at the opposite side in said lower reaction zone IIa; and at least one means providing a vapor passageway disposed vertically at one side and at least one means providing a liquid passageway disposed vertically at the opposite side in said upper reaction zone IIc.

8. An equipment according to claim 7 wherein an upper end of said means providing a liquid passageway disposed vertically in said lower reaction zone IIa is higher than a lowermost distillation tray of said middle distillation zone IIb to provide a weir on the lowermost tray.

9. An equipment according to claim 7, wherein said plurality of trays of said stripping section III includes an uppermost tray and a weir is provided on the uppermost tray of said stripping section for maintaining a liquid layer on said uppermost tray and ensuring a stream of vapor phase flows into the means providing a vapor passageway disposed vertically in said lower reaction zone by disposing a lower end of said means providing a liquid passageway disposed vertically in said lower reaction zone IIa below an upper edge of said weir on the opposite side of said uppermost tray.

10. An equipment according to claim 7, wherein catalyst is packed in bulk into catalyst bed or beds.

11. An equipment according to claim 7, wherein a feed inlet is disposed between each pair of adjacent catalyst beds of said plurality of catalyst beds of the lower reaction zone IIa for introducing unpreheated feed containing reactants.

12. An equipment according to claim 7, wherein an upper end of said means providing a liquid passageway disposed vertically in said upper reaction zone IIc is higher than a lowermost tray of said rectifying section I to provide a weir on said lowermost tray for ensuring a liquid layer on said lowermost tray.

13. An equipment according to claim 7, wherein a weir is provided on said partition, and a lower end of said means providing a liquid passageway disposed in said upper reaction zone is lower than an upper edge of said weir disposed on said partition and a liquid outlet is positioned higher than the lower end of said means providing a liquid passageway disposed in said upper reaction zone IIc to form a liquid seal on said partition.

* * * * *